United States Patent [19]

Langelüddeke et al.

[11] Patent Number: 5,525,578

[45] Date of Patent: Jun. 11, 1996

[54] HERBICIDAL AGENTS CONTAINING IMIDAZOLE HERBICIDE AND ETHER SULFATE SURFACTANTS

[75] Inventors: Peter Langelüddeke; Jean Kocur, both of Hofheim am Taunus; Walter Dannigkeit, Kelkheim/Taunus, all of Germany

[73] Assignee: Hoechst Aktiengesellschaft, Frankfurt, Germany

[21] Appl. No.: 345,867

[22] Filed: Nov. 28, 1994

Related U.S. Application Data

[63] Continuation of Ser. No. 201,056, Feb. 24, 1994, abandoned, which is a continuation of Ser. No. 847,079, Jul. 16, 1992, abandoned, filed as PCT/EP90/01898, Nov. 13, 1990, published as WO91/07089.

[30] Foreign Application Priority Data

Nov. 21, 1989 [DE] Germany ............... 39 38 564.7

[51] Int. Cl.⁶ ................. A01N 43/40; A01N 43/54; A01N 57/12
[52] U.S. Cl. .................. 504/128; 504/139; 504/130; 504/116; 71/DIG. 1
[58] Field of Search ............... 504/116, 127, 504/128, 130

[56] References Cited

U.S. PATENT DOCUMENTS 4,400,196  8/1983  Albrecht et al. ............... 71/86

FOREIGN PATENT DOCUMENTS

| 31433/89 | 9/1989 | Australia . |
|---|---|---|
| 0048436 | 3/1982 | European Pat. Off. . |
| 252237 | 5/1986 | European Pat. Off. . |
| 336151 | 3/1988 | European Pat. Off. . |
| 2833274 | 7/1989 | Germany . |

*Primary Examiner*—Richard L. Raymond
*Assistant Examiner*—Brian G. Bembenick
*Attorney, Agent, or Firm*—Curtis, Morris & Safford

[57] ABSTRACT

The agents according to the invention which contain
a) herbicides selected from the group of the imidazolinones of the formula (I) and (II) as claimed in claim 1 and, if desired, additionally phosphinothricin or known analogs,
b) $C_{10}$–$C_{18}$-fatty alcohol polyglycol ether sulfates as wetting agents and
c) customary additives, permit a surprisingly lower application rate of active ingredient compared with herbicidal agents without wetting agent b, while having the same effectiveness.

10 Claims, No Drawings

HERBICIDAL AGENTS CONTAINING IMIDAZOLE HERBICIDE AND ETHER SULFATE SURFACTANTS

This application is a continuation of application Ser. No. 08/201,056, filed Feb. 24, 1994, now abandoned which is a continuation of Ser. No. 05/847,079, filed Jul. 16, 1992, now abandoned.

DESCRIPTION

It is known that the active substance glufosinateammonium (1)

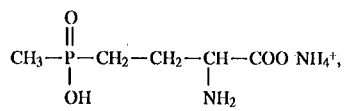

i.e. the ammoniumsalt of 4-[hydroxy(methyl)phosphinoyl]-DL-homoalanine, can be used as a leaf-acting herbicide, namely, for example, for the non-selective control of weeds in fruit growing and viticulture, in tropical plantation crops, in vegetable growing before drilling or before transplanting, before the direct drilling of maize or soya beans, and on wasteland such as verges, industrial terrain and railway installations (cf. Z. PflKrankh. PflSchutz, Special Edition IX, 431–440, 1981). The active substance mentioned contains an asymmetric carbon atom. The formula (1) embraces all stereoisomers and their mixtures, in particular (lacuna) racemate and the biologically active L-enantiomer. The racemate is conventionally applied at dosage rates of between 200 and 1000 grams per hectare (in the form of the formulated product containing 200 g of a.i./l). At these dosage rates, glufosinate-ammonium is only effective if it is taken up via the green parts of the plant. Since it is microbially degraded in the soil in a few days, it has no permanent action whatsoever in the soil. This also applies in a similar way to the related active substance bialaphos (sodiumsalt of 2-L-amino-4-[hydroxy(methyl)phosphinoyl)butanoylalanylalanine) of the formula (2)

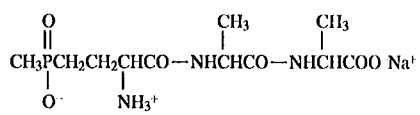

Furthermore, it is known that the active substance imazapyr, 2-(4-isopropyl-4-methyl-5-oxo-2-imidazolin-2-yl)-nicotinic acid which belongs to the chemical group of the imidazolinones, can be used in the form of the isopropylamine salt of the formula (3)

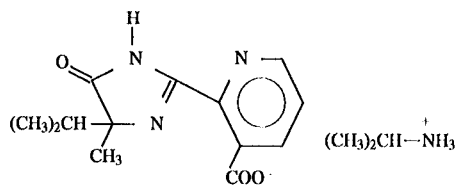

as a total herbicide for various indications (10th Internat. Congr. Plant Protection, 339 et seq., 1983). This active substance can be taken up by the plant via green parts of the plant such as leaf or stalk and also via subterranean parts such as roots or rhizomes. It is known for its long action, on the one hand, and, on the other hand, for the fact that its degradation rate in the soil is slow, so that, in consequence, it remains active in the soil over a long time. It is customarily employed on wasteland at dosage rates of between 250 and 1000 g/ha. On areas under cultivation, imazapyr can only be used as an exception since even low dosage rates, for example 125 g/ha, damage most crop plants.

Active substances of the same chemical group, such as, for example,

Imazamethabenz, i.e. methyl 6-(4-isopropyl-4-methyl-5-oxo-2-imidazolin-2-yl-m, p-toluenecarboxylate, Imazaquin, i.e. 2-(4,5-dehydro-4-methyl-4-(1-methylethyl)-5-oxo-1-H-imidazol-2-yl)-3-quinolinecarboxylic acid, or Imazethapyr, i.e. (+)-5-ethyl-2-(4-isopropyl-4-methyl-5-oxo-2-imidazolin-2-yl)-nicotinic acid, have a similar type of action, but can also be used in some crops for the selective control of weeds.

Because of the particularly high water-solubility of the active substance imazapyr (62–65%, information provided by manufacturers), there is danger of leaching of the active substance after heavy rainfalls and, mainly, on light soils whose sorption capacity is low, in particular when substantial amounts are applied.

It is furthermore known that the action of glufosinateammonium and that of its L-enantiomer can be markedly improved by a substantial number of surface-active substances, preferably by wetting agents such as alkyl polyglycol ether sulfates, which are preferably used in the form of their alkali or ammonium salts, but also as the magnesium salt, for example sodium $C_{12}/C_{14}$ fatty alcohol diglycol ether sulfate, such as ®Genapol LRO (cf. EP-A-0,048,436 or U.S. Pat. No. 4,400,196, and EP-A 0,336,151, and also EWRS Symp. "Factors Affecting Herbicidal Activity and Selectivity", 227–232 (1988)). In the examples which follow, this substance is termed Wetting Agent A.

EP-A 0,252,237 discloses that synergism is possible when glufosinate-ammonium and imazapyr are combined, the application rates used, however, being kept within the range of the abovementioned quantities.

Surprisingly, it has now been found in further experiments that the application rate of imazapyr or its analogs or certain glufosinate/imazapyr combinations or analog herbicide combinations, which is required for a sufficient action, can surprisingly (sic) be markedly reduced when used against various weeds by adding a wetting agent of the type mentioned.

The invention relates to herbicidal agents which have an effective content of a) one or more herbicides of the formulae (I) and (II) or salts thereof

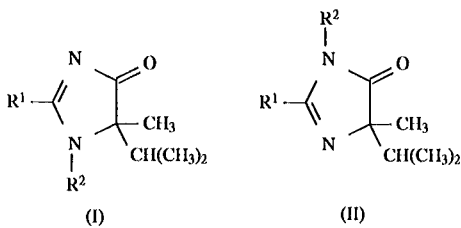

where $R^1$ is phenyl, pyridyl or quinolinyl, each of which is optionally mono- polysubstituted (sic) by $(C_1-C_4)$alkyl, $(C_1-C_4)$alkoxy, $(C_1-C_4)$haloalkyl, $(C_1-C_4)$haloalkoxy, a radical of the formulae —COOR³, —COO—CHR³—COOR³, —CHR³—COO$(C_1-C_4$-alkyl) or —CHR³—COOCHR³—COOR³, where in each case independently of one another R³ radicals are H or $(C_1-C_4)$alkyl, or by a radical of the formula —CH₂—S(O)$_n$—$(C_1-C_4)$-alkyl where n is 0, 1 or 2, and $R^2$ is H, or a radical of the formula —$CONH(C_1-C_4\text{-alkyl})$; —$OCO(C_1-C_4\text{alkyl})$ or —$CO(C_1-C_4\text{-alkyl})$, or a combination of one or more compounds of the formula (I) or (II) with one or more compounds of the formula (III) or salts thereof,

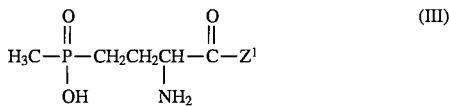

where $Z^1$ is a radical of the formula —OM, —$NHCH(CH_3)CONHCH(CH_3)COOM$ or —$NHCH(CH_3)CONHCH[CH_2CH(CH_3)_2]COOM$ in which M in each case is hydrogen or an inorganic or organic cation, in a ratio by weight of 1:3 to 1:30 of the compounds of the formula (I) or (II) to compounds of the formula (III), b) anionic wetting agents from the group of the $C_{10}-C_{18}$-fatty alcohol polyglycol ether sulfates in the form of the alkali metal salts, ammonium salts or alkaline earth metal salts or of the ammonium salts which are substituted by alkyl or hydroxyalkyl groups, and c) if appropriate, customary inert additives.

Herbicidal agents which are of particular interest are those which have an effective content of a) one or more herbicides selected from the group comprising imazapyr, imazaquin, imazamethabenz and imazethapyr and the salts thereof, or a combination of one or more of the herbicides selected from the group comprising imazapyr, imazaquin, imazamethabenz and imazethapyr, and the salts thereof, with one or more of the herbicides selected from the group comprising glufosinate and bialaphos, and the salts thereof, in a ratio by weight of 1:3 to 1:30, preferably 1:3 to 1:15, b) anionic wetting agents selected from the group of the anionic wetting agents mentioned, and c) inert additives.

Preferred herbicidal agents according to the invention are those in which component a) is imazapyr-isopropylammonium or a combination of glufosinate-ammonium with imazapyr-isopropylammonium in a ratio by weight of 10:1 to 3:1.

Preferred anionic wetting agents are sodium salts of $C_{10}-C_{18}$-fatty alcohol polyglycol ether sulfates.

The compounds of the formulae (I) to (III) are known (see EP-A-0,252,237 and the references cited therein; cf. also "The Pesticide Manual", British Crop Protection Council, 8th edition, 1987). They also embrace all stereoisomers including the pure enantiomers which are possible, and mixtures thereof.

In the event that $R^2$ is H, the two formulae (I) and (II) are in an equilibrium of tautomers. Depending on the radicals $R^2$ and the remaining substituents, there can therefore exist one or the other form (I or II) or a mixture of the two forms, see DE-A 3,121,636 and DE-A 2,833,274.

The compounds of the formulae (I) to (III) which are employed according to the invention also embrace the salts which can be employed in agriculture. Examples of suitable salts are the customary alkali metal salts, alkaline earth metal salts, substituted or unsubstituted ammonium, phosphonium or sulfonium salts. Particular emphasis amongst the alkali metal salts and alkaline earth metal salts must be given to the Na, K, Mg or Ca salts.

Furthermore, the compounds of the formulae (III) also embrace acid-addition salts with inorganic acids such as HCl, HBr, $H_2SO_4$ or $H_3PO_4$, or with organic acids such as $(C_1-C_4)$carboxylic acids, chlorinated acetic acids, tartaric acid or citric acid.

The herbicidal agents according to the invention can be in the form of mixed formulations of the components (active substance+ wetting agent) which are then applied in a customary manner in the form of a dilution with water, or they can be prepared as so-called tank mixes by mixing the unformulated, or separately formulated, active substances with the wetting agent, and diluting the combination with water. If necessary, further wetting agent can be added to the spray liquor before application.

The herbicidal agents can be formulated in various ways, as predetermined by the biological and/or chemicophysical parameters. The following are suitable formulation possibilities: wettable powders (WP), emulsifiable concentrates (EC), aqueous solutions (SL), emulsions, sprayable solutions, dispersions on an oil or water base, suspoemulsions, dusting powders (DP), seed-treatment agents, granules for soil application or for broadcasting (FG), water-dispersible granules (WG), ULV formulations, microcapsules or waxes.

These individual types of formulations are known in principle and are described, for example, in: Winnacker-K üchler, "Chemische Technologie [Chemical Technology]", volume 7, C. Hauser Verlag, Munich, 4th edition, 1986; van Valkenburg, "Pesticides Formulations", Marcel Dekker N.Y., 2nd Ed. 1972–73; K. Martens, "Spray Drying Handbook", 3rd Ed. 1979, G. Goodwin Ltd. London.

Preferred formulations are those in the form of emulsions, aqueous solutions, sprayable solutions, emulsifiable concentrates and water-dispersible granules.

The customary additives which the agents according to the invention can contain are those which are necessary or advantageous for preparing the specific types of formulations.

Customary additives for preparing aqueous solutions and emulsions such as, for example, water, organic solvents and further anionic and non-ionic surfactants, are preferred.

Examples of preferred solvents are alcohols such as methanol, ethanol, propanol, isopropanol, n-, i-, t- and 2-butanol. Preferred surfactants are polyalkylene glycol monoalkyl ethers and polyalkylene glycol dialkyl ethers such as propylene glycol monomethyl ether and propylene glycol monoethyl ether, perfluoroalkyl-containing surfactants such as perfluoro-$(C_6-C_{12})$-alkylphosphinic acids and -phosphonic acids and their alkali metal salts, ammonium salts and alkyl-substituted ammonium salts (for example ®Fluowet PP, Hoechst AG).

In general, the agents according to the invention contain 10 to 95% by weight of component a) and b) and 5 to 90% by weight of customary additives. Aqueous solutions contain preferably 10 to 40% by weight, in particular 15 to 30% by weight, of active substances of component a), 10 to 40% by weight, in particular 25 to 35% by weight, of component b), 30 to 60% by weight of water and 5 to 30% by weight of customary additives, in particular 5–20% by weight of non-ionic surfactants or solvents.

The agents according to the invention act against a broad spectrum of weeds. They are suitable, for example, for controlling annual and perennial weeds such as, for example, inter alia, Agropyron, Paspalum, Cynodon, Imperata, Pennisetum, Convolvulus, Cirsium and Rumex.

The agents according to the invention can be employed for selectively controlling harmful plants in plantation crops such as oil palm, coconut palm, rubber tree, citrus, pineapple, cotton, coffee, cocoa, etc., and in fruit growing and viticulture. The combinations according to the invention can likewise be employed in arable farming using the so-called "no till" or "zero till" method. However, they can also be used non-selectively on paths, squares, industrial terrain etc. so as to keep these areas free from undesired plant growth.

Herbicidal agents according to the invention which do not contain a compound of the formula (III) can be employed, in particular, in wasteland for controlling a broad spectrum of annual and perennial weeds, and in plantations of rubber trees and oil palms; in this context, the application rate of the active substance of the formula (I) and/or (II) can be markedly reduced in comparison with agents without component b) according to the invention. The danger of leaching of the active substance and hence the risk of contaminations of the ground water is likewise reduced.

Herbicidal agents according to the invention which contain a compound of the formula (III) can be employed very advantageously in fruit growing and viticulture, including citrus cultures, in addition to the indications mentioned. One advantage is the fact that an addition of the wetting agent b) results in an acceleration of the uptake of the active substances of the formula (I) or (II) and that relatively low dosage rates of the active substances (I) or (II) and (III) suffice for achieving a good action. Moreover, rain-fastness of the active substances of the formula (III) is also considerably improved. A particular advantage which is important here is that the effective dosage rates, which are used in the combinations, of compounds of the formula (I) and/or (II) are so low that their action via the soil is considerably reduced. This not only makes their application in sensitive crops possible in the first place, but contaminations of the ground water are virtually avoided.

The combination according to the invention of active substances and wetting agents makes possible a considerable reduction of the necessary application rate of the active substances.

The invention therefore also relates to a method of controlling undesired plant growth, which comprises applying, to the plants or the area under cultivation, a) one or more herbicides of the mentioned formulae (I) and/or (II), or salts thereof, or a combination of one or more compounds of the formula (I) and/or (II), or salts thereof, with one or more compounds of the mentioned formula (III) or salts thereof, the ratio by weight of (I) or (II) to (III) in the combination being 1:3 to 1:30, preferably 1:3 to 3:15, together with b) an anionic wetting agent selected from the group of the $C_{10}$–$C_{18}$-fatty alcohol polyglycol ether sulfates in the form of the alkali metal salts, ammonium (sic), alkaline earth metal salts or alkyl- or hydroxyalkyl-substituted ammonium salts.

The application can be effected in such a way that the components are mixed and applied together, or the components are applied in immediate succession in a suitable, separate or partly-separate, formulation.

In general, the application rate is 10 to 400 g/ha, preferably 25 to 200 g/ha, in the case of the compounds of the formula (I) and/or (II), and salts thereof, and 50 to 800 g/ha, preferably 200 to 600 g/ha, in the case of compounds of the formula (III) and salts thereof.

The amount of component b) is generally around 500 to 2500 g/ha, preferably 700 to 1500 g/ha.

FORMULATION EXAMPLES

In the examples which follow, wetting agent A is the sodium salt of $C_{12}/C_{14}$-fatty alcohol) (sic) diethylene glycol ether sulfate (®Genapol LRO, Hoechst AG)

Example 1

To a solution of 11.50 g of imazapyr-isopropylammonium in 48.25 g of water there are added 30 g of wetting agent A (70% strength in $H_2O$) and 10 g of propylene glycol monomethyl ether. The mixture is stirred at 40° C. until a clear solution has formed.

0.25 g of Fluowet PP (80% strength in water) is then added, and stirring is continued for a short time.

Example 2

To a solution of 22.30 g of imazapyr-isopropylammonium in 37.45 g of water there are added 30 g of wetting agent A (70% strength in water) and 10 g of isopropanol. The mixture is stirred until a clear solution has formed.

0.25 g of Fluowet PP (80% strength in water) is then added, and stirring is continued for a short time.

Example 3

To a solution of 18.00 g of glufosinate-ammonium and 2.25 g of imazapyr-isopropylammonium in 39.50 g of water there are added 30.00 g of wetting agent A (70% strength in water) and 10.00 g of propylene monoglycol monomethyl ether. The mixture is stirred at 40° C. until a clear solution has formed.

0.25 g of Fluowet PP (80% strength) is then added, and stirring is continued for a short time.

Example 4

To a solution of 18.00 g of glufosinate-ammonium and 4.50 g of imazapyr-isopropylammonium in 37.25 g of water there are added 30.00 g of wetting agent A (70% strength in water) and 10.00 g of propylene glycol monomethyl ether and 0.25 g of Fluowet PP (80% strength) and the mixture is stirred until a clear solution has formed.

Example 5

To a solution of 9.30 g of L-glufosinate-ammonium and 2.30 g of imazapyr-isopropylammonium in 48.15 g of water there are added 30.00 g of wetting agent A (70% strength in water) and 10.00 g of propylene glycol monomethyl ether. Stirring of the mixture at 40° C. is continued until a clear solution has formed.

0.25 g of Fluowet PP (80% strength) are then added, and stirring is continued for a short time.

USE EXAMPLES

Example 6

For a model experiment, peas were sown in pots (diameter 10 cm) which had been filled with a loam/sand mixture; the pots were subsequently placed in the open until the emerged plants had formed 3 to 4 leaves. They were then treated with imazapyr on its own (in the form of the commercially available preparation ®Arsenal with 250 g of a.c./l; a.c.= acid equivalent) or as a mixture with the wetting agent A (WA A=®Genapol LRO liquid with 290 g/l "detergent"=D, i.e. effective wetting agent). Water was used in amounts of 300 l/ha. 3 to 4 hours after the treatment, some of the pots were exposed to an artifical rain of about 10 mm. The dosage rate of wetting agent was 870 g of SAS/ha. The effect of the treatment can be seen from Table 1 below:

TABLE 1

| Agent and application rate[1] | Action in %[2] No rain | | | |
|---|---|---|---|---|
| | 2 wat | 4 wat | 2 wat | 4 wat |
| Imazapyr | Variant A | | Variant B | |
| 31.25 | 0 | 15 | 0 | 55 |
| 62.5 | 20 | 50 | 20 | 58 |
| 125 | 30 | 53 | 35 | 70 |
| 250 | 37 | 72 | 40 | 83 |
| Imazapyr + WA A | Variant C | | Variant D | |
| 31.25 + 870 | 30 | 65 | 25 | 60 |
| 62.5 + 870 | 50 | 83 | 35 | 70 |
| 125 ± 870 | 55 | 95 | 40 | 85 |
| 250 + 870 | 65 | 98 | 58 | 90 |
| WA A 870 | 0 | 0 | 0 | 0 |

[1] Application rate of imazapyr in g of a.e./ha Application rate of wetting agent A in g of D/ha
[2] Action in % (100 = complete destruction, 0 = no damage), wat = weeks after treatment It is evident from the figures 1. that the action of imazapyr is not very powerful yet after 2 weeks, but, in contrast, considerably more powerful after 4 weeks (variant A);
2. that the action of imazapyr increases after an overhead irrigation treatment (variant B), which can be explained easily by the fact that the active substance which has been washed off the leaf now acts on the plant via the soil;
3. that the initial and the final action of imazapyr increases considerably when wetting agent A is added (variant C);
4. but that, in contrast to variant B, the action of a treatment with imazapyr+ wetting agent is lower with overhead irrigation (variant D) than in variant C without overhead irrigation, but considerably more powerful than in variant B or, especially, in variant A.

This permits the conclusion that uptake of the active substance imazapyr via the leaf is considerably accelerated by an addition of wetting agent A.

Example 7

In a field trial for controlling the perennial weed twitch (Agropyron repens), plots of size 10 m² were treated with various dosage rates and combinations according to the invention of glufosinate-ammonium, imazapyr and wetting agent A, and the effect on the visible green matter was scored by comparison with an untreated control (see Table 2).

Colby's formula was used for assessing the combination action:

$$E = X + Y - \frac{XY}{100}$$

where E is the effect (in %) expected from the combination of the active substance X with the active substance Y (cf. Weeds 15, 20–22, 1967). In the combination treatment, this effect to be expected is given in brackets in front of the effect which was actually achieved. In Table 2, WAA= ®Genapol LRO with 290 g/l detergent, D (dosage in g of D/ha), GLUA= glufosinate-ammonium (dosage in g of a.i./ha ) and IMZP= imazapyr (dosage in a.e./ha). The column under X indicates the number of the tests which were used as a reference for the calculation using Colby's formula.

TABLE 2

| Products and dosage rates | | | | Action in % Weeks after treatment | | |
|---|---|---|---|---|---|---|
| GLUA | IMZP | WA A | X | 4 | 8 | 12 |
| 1. 200 | | | | 60 | 0 | 0 |
| 2. 200 | + | 1000 | | 75 | 10 | 0 |
| 3. 400 | | | | 85 | 25 | 0 |
| 4. 400 | + | 1000 | | 92 | 30 | 0 |
| 5. 600 | | | | 95 | 30 | 0 |
| 6. 600 | + | 1000 | | 95 | 50 | 0 |
| 7. | 25 | | | 10 | 10 | 0 |
| 8. | 25 + | | | 40 | 30 | 10 |
| 9. | 50 | | | 25 | 45 | 35 |
| 10. | 50 + | 1000 | | 45 | 55 | 40 |
| 11. 200 | + 25 | | 1 + 7 | (64) 70 (10) | 20 (0) | 0 |
| 12. 200 | + 25 + | 1000 | 2 + 8 | (85) 91 (37) | 75 (10) | 65 |
| 13. 400 | + 25 | | 3 + 7 | (86.5) 90 (32.5) | 40 (0) | 10 |
| 14. 400 | + 25 + | 1000 | 4 + 8 | (95.2) 95 (51) | 87 (10) | 75 |
| 15. 600 | + 25 | | 5 + 7 | (95.5) 95 (37) | 50 (0) | 15 |
| 16. 600 | + 25 + | 1000 | 6 + 8 | (97) 96 (65) | 90 (10) | 80 |
| 17. 200 | + 50 | | 1 + 9 | (70) 72 (45) | 50 (35) | 40 |
| 18. 200 | + 50 + | 1000 | 2 + 10 | (86.2) 93 (59.5) | 85 (40) | 78 |
| 19. 400 | + 50 | | 3 + 9 | (88.7) 96 (58.7) | 65 (35) | 40 |
| 20. 400 | + 50 + | 1000 | 4 + 10 | (95.6) 96 (68.5) | 92 (40) | 85 |
| 21. 600 | + 50 | | 5 + 9 | (96.2) 98 (61.5) | 72 (35) | 45 |
| 22. 600 | + 50 + | 1000 | 6 + 10 | (97.2) 99 (77.5) | 95 (40) | 90 |

The conclusions from this experiment are:

1. Glufosinate-ammonium dosage rates of 200 to 600 g/ha result in a relatively rapid visible action; in some cases, the scores 2 weeks after the treatment were even higher than the values for 4 weeks after the treatment, shown in Table 2. The action was slightly improved by adding the wetting agent; this was evident even 8 weeks after the treatment when the new growth from the perennial organs in the soil, the rhizomes, was assessed; however, 4 weeks later the stand has regenerated completely and no action whatsoever can be detected.

2. As expected, imazapyr treatments with 25 or 50 g/ha had only a very slight action which, however, was improved by adding the wetting agent.

3. 4 weeks after the treatment, the combinations of glufosinate-ammonium+ imazapyr had a similar effectiveness as glufosinate-ammonium on its own, or only slightly better. A markedly better action which was above the action to be expected was revealed 8 weeks after the treatment, but was lost again 12 weeks after the application.

4. In contrast, if the Wetting Agent A was added to the mixture mentioned, the scores (lacuna) 8 and 12 weeks were markedly higher, in some cases substantially higher, than the values which would have been expected using Colby's formula on the basis of the action of the individual active substances. Assuming that the action via the soil, of the relatively low imazapyr dosage rates, is independent on the wetting agent, it can be concluded that imazapyr uptake via the leaf and the translocation to the subterranean parts was considerably improved by adding the wetting agent, which was surprising.

Example 8

In a 3-year old apple plantation, various treatments were effected in the rows of the trees in spring, at the end of April; the weeds which occurred were mainly various perennial grasses and, inter alia, thistles (*Cirsium arvense*), and ground ivy (*Glechoma hederacea*). (lacuna) effect on the weeds and the compatibility with the crop plants were recorded at intervals. The apple trees did not come in contact with the spray liquor (see Table 3).

TABLE 3

| Products and dosages in g of a.i./ha, a.c./ha and g of D/ha | | | Action (%) | | Damage | |
|---|---|---|---|---|---|---|
| Gufosinate-ammonium | Imazapyr | WA A | 2* | 3* | 2* | 3* |
| 500 | 125 | | 80 | 85 | marked | |
| 500 | 125 | 1000 | 95 | 98 | damage | |
| 500 | 50 | | 50 | 55 | no | |
| 500 | 50 | 1000 | 90 | 85 | damage | |

*months after treatment

As expected, the action (sic) of combinations with a higher proportion of imazapyr were more effective over a longer period of time, the variant with an addition of wetting agent performing even better than those without wetting agent. However, in both treatment variants, marked damage on the shoot tips of the trees occurred after 1.5 to 2 months, which led to a standstill of growth; the symptoms corresponded to normal imazapyr symptoms, the active substance obviously having been taken up via the root (sic).

If the application rate of imazapyr was reduced, the development of the weeds diminished to such an extent that it was (sic) insufficient 2-3 months after the treatment. However, damage occurred no longer in this case. The same herbicide combination with an addition of wetting agent resulted in a considerably improved action against weeds, which could be assessed as satisfactory even 3 months later. In this treatment, damage to the trees was not observed either.

Example 9

In a field trial in (sic) barley as a monocotyledon test plant, plots were treated with glufosinate-ammonium in combination with very small amounts of imazapyr, with and without the addition of Wetting Agent A. At the point of time when the treatment was effected, the plants were in the tillering phase. The amount of water applied was about 300 l/ha. 3 hours after application, some of the plots were exposed to an artificial overhead irrigation of about 10 mm. The result in the form of score figures two weeks after the treatment is shown in Table 4.

TABLE 4

| Products and dosages in g of a.i./ha, g of a.c./ha and g of D/ha | | | without | with |
|---|---|---|---|---|
| Glufosinate-ammonium | Imazapyr | wetting agent A | overhead irrigation | overhead irrigation |
| 500 | 0 | 0 | 90 | 20 |
| 500 | 0 | 1000 | 95 | 45 |
| 0 | 20 | 0 | 0 | 0 |
| 0 | 20 | 1000 | 0 | 0 |
| 500 | 20 | 0 | 92 | 50 |
| 500 | 20 | 1000 | 95 | 85 |

The result shows that glufosinate on its own or glufosinate plus wetting agent showed good effectiveness, and that the action in both variants declined very rapidly when an overhead irrigation was carried out 3 hours after the treatment, the decline being not quite as pronounced when a wetting agent was added. By no means however was the action sufficient for conditions encountered in practice. Low amounts of 20 g/ha was without effect, without and with the addition of wetting agents. Glufosinate-ammonium plus imazapyr were very effective, in contrast, the action in the plot with overhead irrigation was entirely insufficient. Only in the treatment according to the invention, the combination glufosinateammonium plus imazapyr plus wetting agent A, was the action so good even in the plot with overhead irrigation that it could be called satisfactory under conditions encountered in practice.

Similar results can also be achieved when, in place of glufosinate-ammonium, its L-enantiomer or, alternatively, the active substance bialaphos is used. Likewise, the active substance imazapyr in such combinations can be replaced by another active substance from the same group, for example imazamethabenz, imazaquin or imazethapyr.

We claim:

1. A herbicidal agent with an effective content of
  a) a combination of one or more herbicides of the formulae (I) and (II) or salts thereof

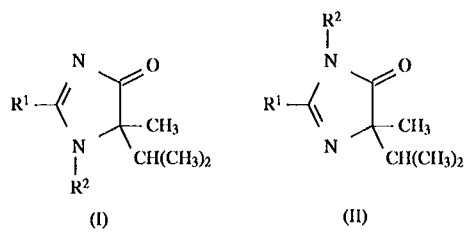

(I)            (II)

where $R^1$ is phenyl, pyridyl or quinolinyl, each of which is optionally monosubstituted or polysubstituted by $(C_1-C_4)$alkyl, $(C_1-C_4)$alkoxy, $(C_1-C_4)$haloalkyl, $(C_1-C_4)$haloalkoxy, a radical of the formulae —$COOR^3$, —COO—$CHR^3$—$COOR^3$, —$CHR^3$—COO$(C_1-C_4$-alkyl) or —$CHR^3$—COOCHR$^3$—$COOR^3$, where in each case independently of one another $R^3$ radicals are H or $(C_1-C_4)$alkyl, or by a radical of the formula —CH$_2$—S(O)$_n$—(C$_1$–C$_4$)-alkyl where n is 0, 1 or 2, and R$^2$ is H, or a radical of the formula —CONH(C$_1$–C$_4$-alkyl); —OCO(C$_1$–C$_4$alkyl) or —CO(C$_1$–C$_4$-alkyl), with one or more compounds of the formula (III) or salts thereof,

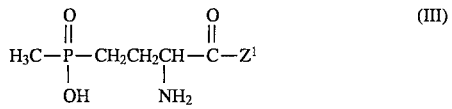

(III)

where

Z$^1$ is a radical of the formula —OM, —NHCH(CH$_3$)CONHCH(CH$_3$)COOM or —NHCH(CH$_3$)CONHCH[CH$_2$CH(CH$_3$)$_2$]COOM in which M in each case is hydrogen or an inorganic or organic cation, in a ratio by weight of 1:3 to 1:30 of the compounds of the formula (I) or (II) to compounds of the formula (III), b) anionic wetting agents from the group of the C$_{10}$–C$_{18}$-fatty alcohol polyglycol ether sulfates in the form of the alkali metal salts, ammonium salts or alkaline earth metal salts or of the ammonium salts which are substituted by alkyl or hydroxyalkyl groups, and c) if appropriate, customary inert additives.

2. A herbicidal agent as claimed in claim 1, which has an effective content of a) a combination of one or more of the herbicides selected from the group consisting of imazapyr, imazaquin, imazamethabenz and imazethapyr, and the salts thereof, with one or more of the herbicides selected from the group consisting of glufosinate and bialaphos, and the salts thereof, in a ratio by weight of 1:3 to 1:30, preferably 1:3 to 1:15, b) anionic wetting agents selected from the group of the anionic wetting agents mentioned, and c) inert additives.

3. A herbicidal agent as claimed in claim 1, in which the component a) is a combination of glufosinate-ammonium with imazapyrisopropylammonium in a ratio by weight of 10:1 to 3:1.

4. A herbicidal agent as claimed in claim 1, in which the component b) is a sodium salt of C$_{10}$–C$_{18}$-fatty alcohol polyglycol ether sulfate.

5. A method of controlling undesired plant growth, which comprises applying, to the plants or the area under cultivation, a) one or more herbicides of the mentioned formulae (I) and (II), or salts thereof, or a combination, as defined in claim 1, of one or more compounds of the formula (I) and/or (II), or salts thereof, with one or more compounds of the mentioned formula (III) or salts thereof, the ratio by weight of (I) or (II) to (III) in the combination being 1:3 to 1:30, preferably 1:3 to 3:15, together with b) an anionic wetting agent selected from the group of the C$_{10}$–C$_{18}$-fatty alcohol polyglycol ether sulfates in the form of the alkali metal salts, ammonium salts, alkaline earth metal salts or alkyl- or hydroxyalkyl-substituted ammonium salts.

6. The method as claimed in claim 5, wherein the application rate of compounds of the formula (I) or (II), or salts thereof, is 10 to 400 g/ha.

7. The method as claimed in claim 5, wherein the application rate of compounds of the formula (III) is 50 to 800 g/ha.

8. The method as claimed in claim 5, wherein the application rate of component b) is 500 to 2500 g/ha.

9. A herbicidal agent as claimed in claim 3 in which the component b) is a sodium salt of C$_{10}$–C$_{18}$-fatty alcohol polyglycol ether sulfate.

10. A method as claimed in claim 5, wherein the application rates are 25 to 200 g/ha of compounds of formula (I) and (II); 200 to 600 g/ha of compounds of formula (III) and 700 to 1500 g/ha of component b).

* * * * *